(12) United States Patent
Alshamar

(10) Patent No.: US 11,885,724 B2
(45) Date of Patent: Jan. 30, 2024

(54) STAIN FOR STAINING CELLS, THE USE OF THE STAIN IN HISTOLOGICAL APPLICATIONS AND A METHOD OF DIAGNOSIS

(71) Applicant: United Arab Emirates University, Al Ain (AE)

(72) Inventor: Hayfaa Abd Ali Mohammed Alshamar, Al Nasiriyah (IQ)

(73) Assignee: United Arab Emirates University, Al Ain (AE)

( * ) Notice: Subject to any disclaimer, the term of this patent is extended or adjusted under 35 U.S.C. 154(b) by 514 days.

(21) Appl. No.: 16/816,892

(22) Filed: Mar. 12, 2020

(65) Prior Publication Data

US 2020/0209119 A1 Jul. 2, 2020

Related U.S. Application Data

(63) Continuation of application No. 15/913,205, filed on Mar. 6, 2018, now abandoned.
(Continued)

(51) Int. Cl.
*G01N 1/30* (2006.01)
*G01N 33/52* (2006.01)
(Continued)

(52) U.S. Cl.
CPC .......... *G01N 1/30* (2013.01); *G01N 33/5091* (2013.01); *G01N 33/52* (2013.01); *G01N 33/574* (2013.01); *G01N 2001/302* (2013.01)

(58) Field of Classification Search
CPC .. G01N 1/30; G01N 2001/302; G01N 33/574; G01N 33/5091; G01N 33/52
See application file for complete search history.

(56) References Cited

U.S. PATENT DOCUMENTS

| 2009/0004304 A1* | 1/2009 | Ikehara | A23L 33/19 424/754 |
| 2013/0281548 A1* | 10/2013 | Jin | A61K 8/731 514/777 |
| 2013/0302852 A1 | 11/2013 | Barnes | |

OTHER PUBLICATIONS

Al-Awwadi, Najim A., et al., "Extracts Enriched in Different Polyphenolic Families Normalize Increased Cardiac NADPH Oxidase Expression while Having Differential Effects on Insulin Resistance, Hypertension, and Cardiac Hypertrophy in High-Fructose-Fed Rats," J. Agric. Food Chem., 2005, 53, 151-157.
(Continued)

*Primary Examiner* — Blaine Lankford
*Assistant Examiner* — Lauren K Van Buren
(74) *Attorney, Agent, or Firm* — Fitch, Even, Tabin & Flannery LLP

(57) ABSTRACT

A staining composition for staining cells and for use in a method of staining cells, a method of diagnosing mitotic activity and a method of diagnosing cancer. The composition comprises dried petunia petals at least partially dissolved in distilled water; and 400 milligrams of picric acid per gram of dried petunia petals. The method of staining cells includes rinsing a sample containing the cells with 10% of phosphotungistic acid or 10% of phosphomolybdic acid; staining the sample with the composition and dehydrating the samples with 100% Ethanol or Isopropanol. The method of diagnosing mitotic activity includes observing stained regions in the sample to identify mitotic activity indicated by stained regions. The method for diagnosing cancer includes quantifying mitotic figures in the sample which are identified by stained regions of the sample.

9 Claims, 13 Drawing Sheets
(12 of 13 Drawing Sheet(s) Filed in Color)

Related U.S. Application Data

(60) Provisional application No. 62/467,436, filed on Mar. 6, 2017.

(51) Int. Cl.
  *G01N 33/50* (2006.01)
  *G01N 33/574* (2006.01)

(56) References Cited

OTHER PUBLICATIONS

Suvarna, S. Kim, et al., "Bancroft's Theory and Practice and Practice of Histological Techniques," Churchill Livingstone Elsevier, 2013, 604 pages.

Cohen-Boulakia, Francine, et al., "In Vivo Sequential Study of Skeletal Muscle Capillary Permeability in Diabetic Rats: Effect of Anthocyanosides," Metabolism, 2000, vol. 49, No. 7, 880-885.

Da Costa, Cristina, et al., "Separation of blackcurrant anthocyanins by capillary zone electrophoresis," Journal of Chromatography A, 1998, 799, 321-327.

Duthie, Garry G., et al., "Plant polyphenols in cancer and heart disease: implications as nutritional antioxidants," Nutrition Research Reviews, 2000, 13, 79-106.

Fleschhut, Jens, et al., "Stability and biotransformation of various dietary anthocyanins in vitro," Eur J Nutr, 2006, 45, 7-18.

Galvano, Fabio, et al., "Cyanidins: metabolism and biological properties," Journal of Nutritional Biochemistry, 2004, 15, 2-11.

He, Jian, et al., "Anthocyanins: Natural Colorants with Health-Promoting Properties." Annu. Rev. Food Sci. Technol., 2010, 1, 163-87.

Heredia, F.J., et al., "Chromatic characterization of anthocyanins from red grapes—I. pH effect," Food Chemistry, 1998, vol. 63, No. 4, 491-498.

Hollman, P.C.H., et al., "Dietary Flavonoids: Intake, Health Effects and Bioavailability," Food and Chemical Toxicology, 1999, 37, 937-942.

Ames, Bruce N., et al., "Oxidants, antioxidants, and the degenerative diseases of aging," Proc. Natl. Acad. Sci. USA, 1993, vol. 90, 7915-7922.

Kennedy, James A., et al. "Analysis of pigmented high-molecular-mass grape phenolics using ion-pair, normal-phase high-performance liquid chromatography," Journal of Chromatography A, 2000, 866, 25-34.

Luger, Karolin, et al., "Crystal structure of the nucleosome core particle at 2.8 A°resolution," Nature, 1997, 389, 251-260.

Morimitsu, Yasujiro, et al., "Inhibitory effect of anthocyanins and colored rice on diabetic cataract formation in the rat lenses," International Congress Series, 2002, 1245, 503-508.

Stintzing, Florain C., et al., "Color and Antioxidant Properties of Cyanidin-Based Anthocyanin Pigments," J. Agric. Food Chem., 2002, 50, 6172-6181.

Swain, T., et al., "Flavonoid Compounds," Comparative Biochemistry, vol. 3 Constituents of Life. 1962, 755-809.

Einbond, Linda S., et al., "Anthocyanin antioxidants from edible fruits," Food Chemistry, 2004, 84, 23-28.

Ghosh, Dilip., et al., "Cytoprotective effects of anthocyanins and other phenolic fractions of Boysenberry and blackcurrant on dopamine and amyloid β-induced oxidative stress in transfected COS-7 cells," J Sci Food Agric, 2007, 87, 2061-2067.

Jayaprakasam, Bolleddula, et al., "Insulin Secretion by Bioactive Anthocyanins and Anthocyanidins Present in Fruits," J. Agric. Food Chem., 2005, 53, pp. 28-31.

Kumara, N.T.R.N., et al., "Study of the Enhancement of Cell Performance of Dye Sensitized Solar Cells Sensitized With Nephelium lappaceum (F: Sapindaceae)," Journal of Solar Energy Engineering, 2013, 135: 1-5.

Lee, Jonghyun, et al., "Purified high-dose anthocyanoside oligomer administration improves nocturnal vision and clinical symptoms in myopia subjects," British Journal of Nutrition, 2005, 93, 895-899.

Tanwar, Beenu, et al., "Flavonoids: Dietary occurrence and health benefits," Spatula DD, 2012, 2, 1, 59-68.

Levy, Y., et al., "The effect of anthocyanosides on night vision," Eye, 1998, 12, 967-969.

Dapson et al. "Hematoxylin shortages: their causes and duration, and other dyes that can replace hemalum in routine hematoxylin and eosin staining", Biotechnic and Histochemistry, 2010.

Guerra et al. "Hematoxylin: a simple, multiple-use dye for chromosome analysis", Genet. Mol. Biol., vol. 22, 1999.

* cited by examiner

STAIN FOR STAINING CELLS, THE USE OF THE STAIN IN HISTOLOGICAL APPLICATIONS AND A METHOD OF DIAGNOSIS

CROSS REFERENCE TO RELATED APPLICATION

This application is a continuation of U.S. application Ser. No. 15/913,205 filed on Mar. 6, 2018, which claims priority from U.S. Provisional Application No. 62/467,436, filed Mar. 6, 2017, the contents of which are incorporated herein by reference in their entireties.

FIELD OF INVENTION

The invention relates to a stain for staining cells and fibers. The invention relates further to the use of the stain in histological applications and to a method of diagnosis using the stain.

BACKGROUND TO INVENTION

Determination of the mitotic index of all types of cancers using sections stained with routine stain such as, for example, haematoxylin and eosin (H&E) is difficult. Furthermore, sections stained with immunostains or immunohistochemistry stains, such as, for example Ki67 is expensive and time-consuming.

Counting mitotic figures (MFs) is essential for determining the histologic grade of a carcinoma and for diagnosis and prognosis of carcinomas.

A need therefore exists for a method of staining cells which is simple to execute, more specifically, when compared with routine histological stain such as, for example, haematoxylin and eosin (H&E). A need further exists for a method of staining cells which is cheaper when compared to the cost of known methods of staining cells, such as, for example, staining with immunohistochemistry stains, such as, for example ki67

A need further exists for a method of staining cells which is simple to execute and not time consuming when compared to known methods of staining cells, such as, immunohistochemistry stains, such as, for example, Ki67.

A need also exists for a stain and a staining method which only stains the mitotic nuclei of cells and which does not stain the nuclei without mitotic activity, thereby to allow the counting of MFs and to facilitate diagnosis, prognosis and determination of the histological grade of a carcinoma.

A need further exists for a stain which stains collagen fibers and skeletal muscle striations.

In this specification the term "stain" shall be interpreted sufficiently broadly to include a dye. Furthermore, the terms "flowers" and "petals" shall be interpreted sufficiently broadly to include other parts of the plant as well.

SUMMARY OF INVENTION

According to a first aspect of the invention there is provided a stain for staining one or more cells, the stain being obtained from petunia flowers, that is flowers from the genus *Petunia*. The stain may, more particularly, be used for staining a mitotic nucleus of a cell. More specifically, the stain may include an extract obtained from petunia flowers. The extract may be obtained from dry petals of petunia flowers. In one embodiment, the stain may include petunia petals dissolved in a solvent or in a suitable aqueous medium, the stain further including picric acid. In a particular embodiment, the petunia petals may be dried petunia petals. The solvent may be water.

According to a second aspect of the invention there is provided a stain for indicating mitotic activity in a cell, the stain being obtained from petunia flowers. The stain may, more particularly, be used for staining a mitotic nucleus of a cell. More specifically, the stain may include an extract obtained from petunia flowers. The extract may be obtained from dry petals of petunia flowers. In a particular embodiment, the stain may include petals of petunia flowers dissolved in a solvent or in a suitable aqueous medium, the stain further including picric acid. In a particular embodiment, the petunia petals may be dried petunia petals.

According to a third aspect of the invention there is provided a method of diagnosing mitotic activity in a cell, the method including staining the cell with an extract obtained from petunia flowers. The extract may be obtained from dry petals of petunia flowers. More specifically, the method may include staining the cell with a stain including petals of petunia flowers dissolved in a solvent or in a suitable aqueous medium, the stain further including picric acid. In a particular embodiment, the petunia petals may be dried petunia petals. The method may be used for diagnosing cancers, such as, breast cancer and other types of cancer.

According to a fourth aspect of the invention there is provided a staining composition for staining one or more cells, the staining composition comprising:
an extract obtained from petunia petals; and a solution of picric acid.

The extract obtained from petunia petals may, more particularly, comprise petunia petals at least partially dissolved in a solvent or in a suitable aqueous medium. In a particular embodiment, the petunia petals may be dried petunia petals. More specifically, the dried petunia petals may be obtained by providing a predetermined mass of fresh wet petunia petals and drying the petunia petals until a mass thereof is 90% of said predetermined mass. In other words, the wet petunia petals are dried to form dried petunia petals wherein a mass of the dried petunia petals is 10% of a mass of the wet petunia petals.

The staining composition may comprise at least 60 mg of picric acid per gram of the dried petunia petals. In a preferred embodiment, the staining composition may comprise at least about 200 mg of picric acid per gram of the dried petunia petals.

More specifically, the staining composition may advantageously comprise between about 200 mg to 400 mg of picric acid per gram of the dried petunia petals.

In another embodiment, the dried petunia petals may be particularized. More specifically, the dried petunia petals may be ground into a powder.

In a particular embodiment, the solvent or the suitable aqueous medium may be distilled water.

The staining composition has been found to stain only the mitotic nucleus of cells and no other nuclei. In other words, the staining composition does not stain nuclei which are without mitotic activity. Additionally, in particular embodiments, the staining composition has been found to stain collagen fibers. This staining composition may thus be prepared from petunia flowers that are easily available the world over. The staining composition is particularly useful for staining mitotic figures. More specifically, the staining composition is effective in sufficiently staining the mitotic figures to facilitate accurate counting of the mitotic figures.

According to a fifth aspect of the invention there is provided a method of staining one or more cells including rinsing a sample containing said one or more cells to be stained with diluted phosphotungistic acid or diluted phosphomolybdic acid; and staining the rinsed sample with the staining composition as described and defined hereinabove, in accordance with the fourth aspect of the invention.

In a particular embodiment, the diluted phosphotungistic acid or the diluted phosphomolybdic acid may comprise 10% of phosphotungistic acid or 10% of phosphomolybdic acid, respectively.

In another embodiment, the diluted phosphotungistic acid or the diluted phosphomolybdic acid may comprise 5% of phosphotungistic acid or 5% of phosphomolybdic acid, respectively.

The method may include after staining the rinsed sample with the staining composition, dehydrating the stained samples with 100% Ethanol or Isopropanol.

According to a sixth aspect of the invention there is provided a method of diagnosing mitotic activity in one or more cells, the method including staining said one or more cells in accordance with the method of staining one or more cells as described and defined hereinabove in accordance with the fifth aspect of the invention and observing one or more stained regions of said one or more cells to identify mitotic activity indicated by said one or more stained regions.

According to a seventh aspect of the invention there is provided a method for diagnosing cancer in one or more cells, the method including staining said one or more cells in accordance with the method of staining one or more cells as described and defined hereinabove, in accordance with the fifth aspect of the invention; and quantifying said one or more cells and quantifying mitotic figures which are identified by stained regions of said one or more cells. More particularly, the method includes determining a ratio of total number of cells in the sample to number of cells having mitotic figures. The method further includes comparing the determined ratio to an expected ratio which can be expected from a sample comprising healthy cells of the same type as said one or more cells. More specifically, the method may be an in vitro method of diagnosis.

The invention extends to a method for producing a stain as described and defined herein. The invention extends also to a histological kit or diagnosis kit including the stain as described and defined herein.

The stain described and defined hereinabove has been found to be useful in diagnosis and prognosis of cancers, such as, for example, breast cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features of the invention are described hereinafter by way of a non-limiting example of the invention, with reference to and as illustrated in the accompanying diagrammatic drawings. In the drawings.

DETAILED DESCRIPTION

Method of Preparing Aqueous Extract of the Crude Pigment

An aqueous solution of crude pigment was prepared from dry petunia flowers, more specifically, dried petals of petunia flowers. For example, petals of petunia flowers were picked and immediately weighed so at to make up a 100 g batch of fresh wet petunia flower petals for drying thereof. The 100 g batch of fresh wet petunia flowers were then air dried outdoors in the shade for approximately 48 hours at a temperature of approximately 30° C. More specifically, in order to properly dry the petals, the weight of the dry petals was periodically taken until the weight reached approximately 10 g. As such, the petunia petals were dried until the mass of the fresh wet petunia petals was reduced by 90% due to drying thereof.

For example, the aqueous extract of the crude pigment, was prepared by dissolving 3 g of the dry petals of petunia flowers in 20 to 30 mL of distilled water. In particular, blue and purple colored flowers have been found to provide particularly effective for preparing the crude pigment.

Figure 22:
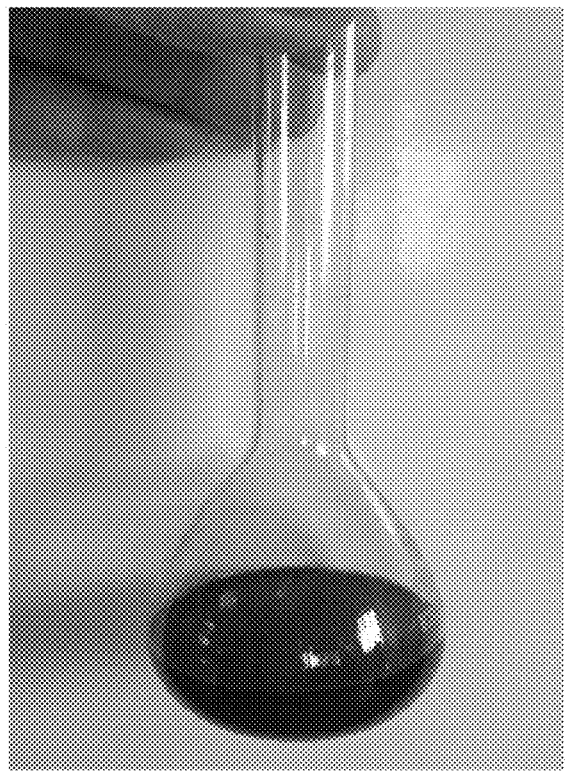
FIG. 22 shows the aqueous solution of dry petals of petunia flowers.
Figure 23:
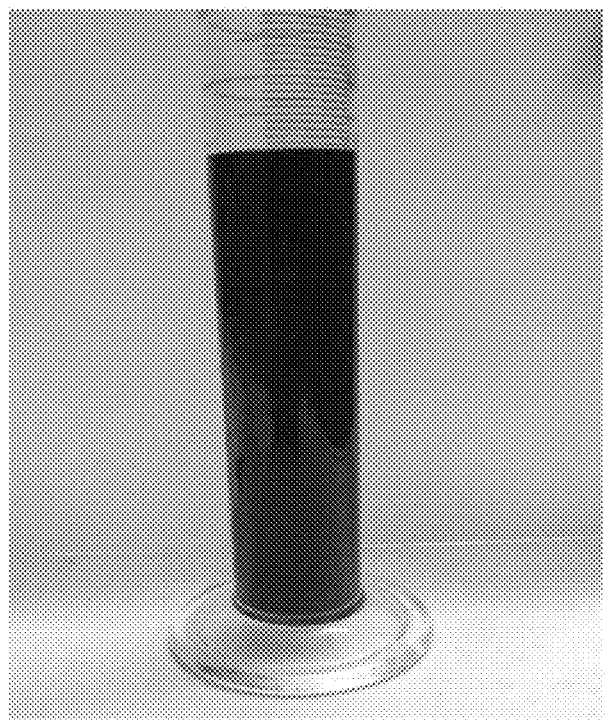
FIG. 23 shows a staining composition comprising a mixture of aqueous solution of dry petals of petunia flowers and saturated picric acid.

Then the volume was made up to 100 mL using a required amount of a 1.2% picric acid solution comprising 1.2 grams of picric acid per 100 mL of distilled water. More specifically, the 1.2% picric acid solution is a saturated solution of picric acid. As illustrated in FIGS. 22 and 23, the color changes from blue (or purple) to red during this process with no precipitate formation.

Tissue Samples to be Stained

Samples of tissues to be stained were obtained from tumors at the time of diagnosis. These included tissues of breast cancer, colon adenosis, and fibro adenosis tumors, fibroadenoma and leiomyoma, Wilms' tumor of the kidney, fibrosarcoma of the abdominal wall, and benign polycystic lesions of the ovary. Additionally, rat tissues, such as those of the liver, kidneys, spleen, small intestine, skin, lachrymal glands, heart, and eyes were obtained.

Preparation of Histological Slides

The sections were prepared according to Luna (Luna, L. G., Manual of Histologic Staining Methods; of the Armed Forces Institute of Pathology, Blakiston Division, McGraw-Hill, 1968, 258 pages) by using the iso propanol as a dehydration agent and chloroform as clearing agent.

To prepare tissue or histological slides, the following steps need to be taken:

1. Fixation: By rinsing the tissue in 10% formalin for 24 hours
2. Dehydration: the tissue is submersed successively in alcohol solutions of increasing concentrations (30-100%).
3. Clearing: by using chloroform.
4. Embedding
   The specimen is submersed into melted wax (the temperature of the wax should be just above its melting point).
5. Section cutting
   A small block of parafin wax containing the tissue is prepared. Using a microtome, around 4-5-μm-thick sections of wax-impregnated tissue are obtained. These wax-impregnated sections are floated on warm water (45° C.); this allows the wax to flatten out then mounted on glass slides (coated with adhesive) and stained.
6. Staining
   Wax is removed from the sections by rinsed in xylene for 10 minutes. The section is rehydrated and stained.
7. Mounting
   After the histological section is stained, a drop of mounting medium is added to the slide and a cover slip is placed on it. Mounting medium commonly used is DPX or Canada balsam.

The following non-limiting examples describe various methods of staining the sections using the stain in accordance with the invention.

Example 1

The aqueous extract of dry petunia flowers and picric acid was mixed together. All the sections were dewaxed, rehydrated then rinsed with 10% of phosphotungistic or 10% phosphomolybdic acid and then stained with the mixed solution of petunia flowers and picric acid. All the sections were investigated under a light microscope at 40× magnification; an oil lens was used for visualizing nuclei.

Example 2

All of the sections were dewaxed, rehydrated, rinsed with 10% phosphotungistic acid or 10% phosphomolybdic acid for 20 to 40 minutes at room temperature and stained with the mixture of aqueous extract of petunia flowers and picric acid at a temperature of 38° C. to 40° C. for 30 to 60 minutes and finally dehydrated with 100% ethanol or iso propanol for a few seconds. All the sections were investigated under a light microscope at 40× magnification; an oil lens was used for visualizing nuclei.

Example 3

All of the sections were dewaxed, rehydrated, rinsed with 10% phosphotungistic acid or 10% phosphomolybdic acid for 20 to 40 minutes at room temperature and stained with the mixture of aqueous extract of petunia flowers and picric acid at a temperature of 38° C. to 40° for 15-30 minutes and finally dehydrated with 100% ethanol or iso propanol for a few seconds. All the sections were investigated under a light microscope at 40× magnification; an oil lens was used for visualizing nuclei.

Example 4

All of the sections were dewaxed, rehydrated, rinsed with 10% phosphotungistic acid or 10% phosphomolybdic acid for 20 to 40 minutes at room temperature and stained with the mixture of aqueous extract of petunia flowers and picric acid at a temperature of 38° C. to 40° C. and finally dehydrated by allowing the sections to dry. The drying can be achieved by air drying for approximately 10 minutes or by dehydrating the sections using 100% ethanol or iso propanol for a few seconds. The sections are then cleared with xylene and covered with DPX (Distyrene Plasticizer Xylene) which is a mountant for use in histology technique.

All the sections were investigated under a light microscope at 40× magnification; an oil lens was used for visualizing nuclei.

Example 5

All of the sections were dewaxed, rehydrated, and rinsed with 10% phosphomolybdic acid or 10% phosphomolybdic acid for 20 to 40 minutes at room temperature and stained with the mixture of aqueous extract of petunia flowers and picric acid at a temperature of 38° C. to 40° C. and finally dehydrated as per the procedures of Examples 2, 3 or 4. All the sections were investigated under a light microscope at 40× magnification; an oil lens was used for visualizing nuclei.

Example 6

All of the sections were dewaxed, rehydrated, rinsed with 5% phosphotungistic acid or 5% phosphomolybdic acid for 20 to 40 minutes at room temperature and stained with the mixture of aqueous extract of petunia flowers and picric acid at a temperature of 38° C. to 40° C. and finally dehydrated by allowing the sections to dry. The drying can be achieved by air drying for approximately 10 minutes or by dehydrating the sections using 100% Ethanol or Isopropanol for a few seconds.

Alternative Methods of Preparing Aqueous Extract of the Crude Pigment

As an alternative to the method of preparing the aqueous extract described hereinabove, unsaturated solutions of 0.6% and 1.5% picric acid have also been found to be advantageous. More specifically 0.6% solutions of picric acid comprise dissolving 200 mg of solid picric acid in 100 ml of distilled water, while 1.5% solutions of picric acid comprise dissolving 1.5 g of solid picric acid in 100 ml of distilled water.

The Applicant has further found that at least 60 mg of picric acid per gram of the dried petunia petals is required.

Findings and Observations

1. Mitotic Figures

This stained samples in FIGS. 1 to 7 of the drawings show that the mitotic figures were characterized by an absent nuclear membrane with clear, hairy extensions of nuclear material (condensed chromosomes) either clumped (early metaphase), in a plane (metaphase/anaphase), or in separate chromosomal aggregates (anaphase/telophase). The cytoplasm of the mitotic cells was often larger than that of the resting cells.

Concentrations of 5% and 10% phosphotungistic acid both gave good results for staining mitotic nuclei of cells, collagen fibers and muscle fibers striation.

Concentrations of 5% and 10% phosphomolybdic acid both gave good results for staining mitotic nuclei of cells and muscle fibers striation.

Concentrations of 5% phosphomolybdic acid only stained mitotic nuclei, but not collagen fibers.

2. Collagen Fibers

Figure 1:
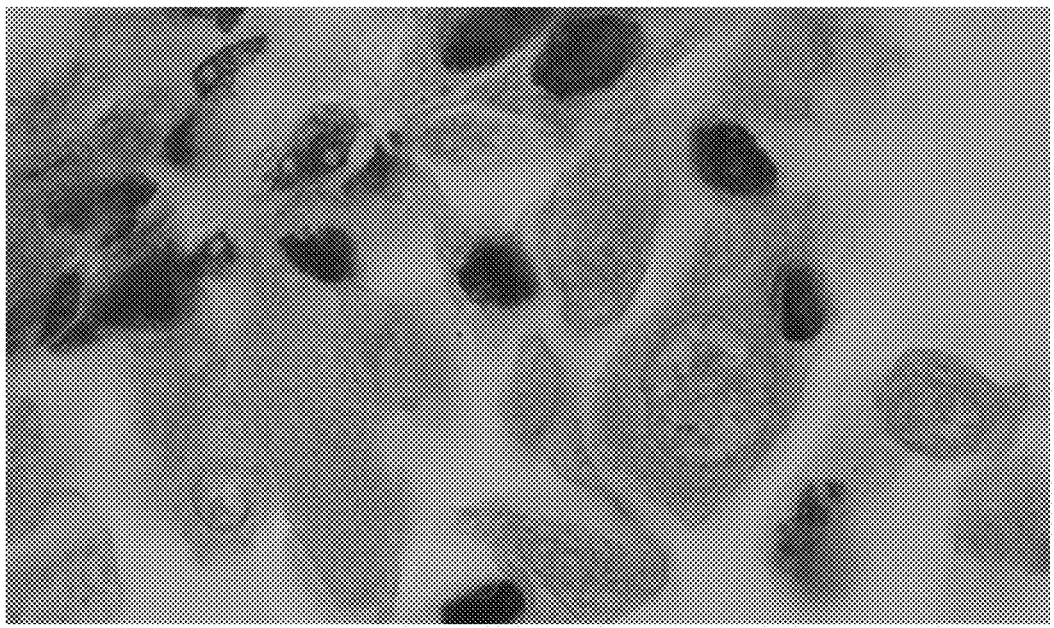
FIG. 1 shows a microscopic image of a number of cells stained in accordance with a method of staining cells in accordance with the invention, the microscopic image shows a number of breast cancer cells nucleus in the interphase (dark) in mitosis (DNA replication) in the S phase, also visible are the nucleus in G1 phase, the microscopic image was captured from a light microscope at 40× magnification using an oil lens.
Figure 2:
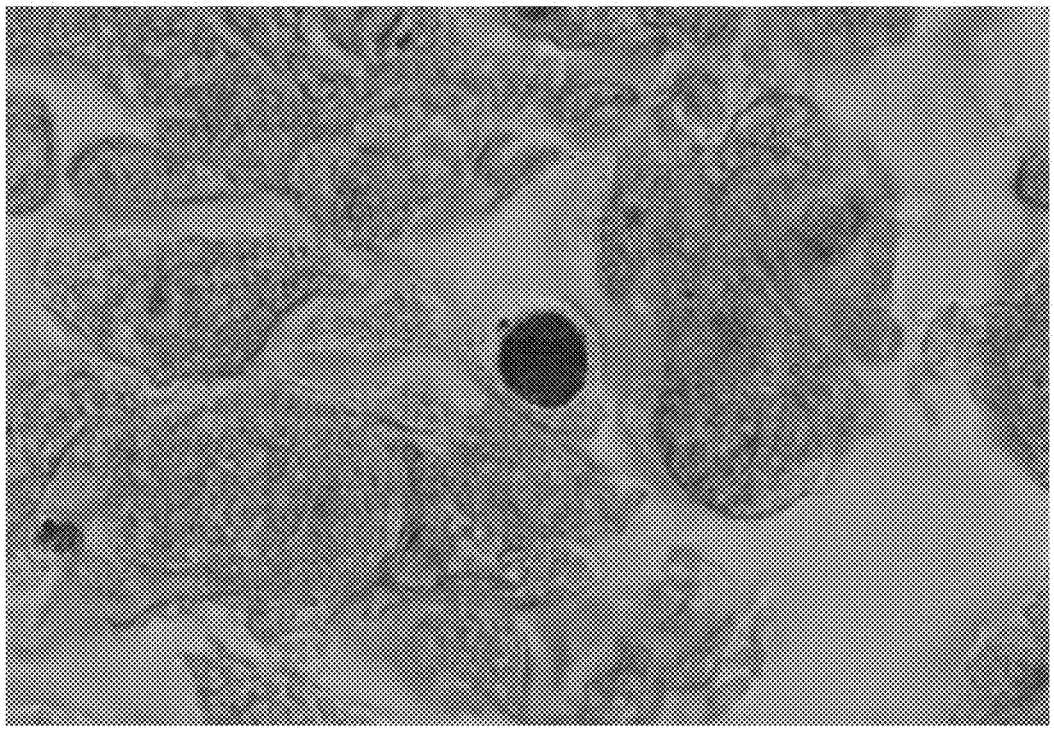
FIG. 2 shows a microscopic image of a number of cells stained in accordance with a method of staining cells in accordance with the invention, the microscopic image shows a nucleus of breast cancer cell in the prophase, also visible are small dark spots which are the centrioles in the mitosis phase, the microscopic image was captured from a light microscope at 40× magnification using an oil lens.
Figure 3:
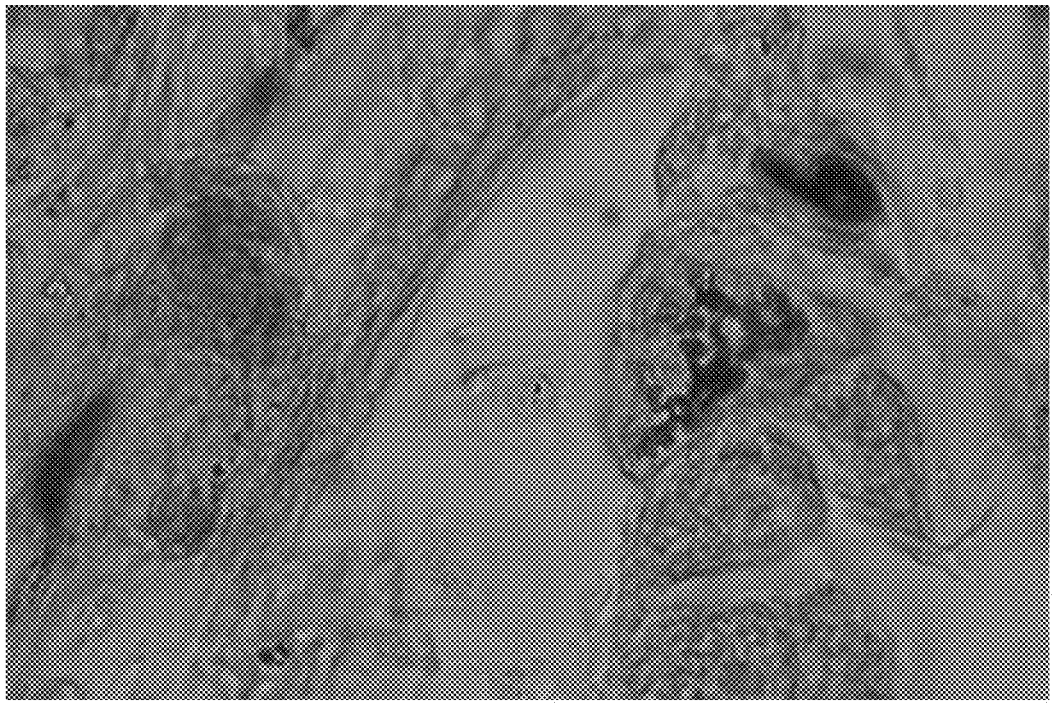
FIG. 3 shows a microscopic image of a number of cells stained in accordance with a method of staining cells in accordance with the invention, the microscopic image shows a nucleus of a breast cancer cell in the metaphase, the microscopic image was captured from a light microscope at 40× magnification using an oil lens.
Figure 4:
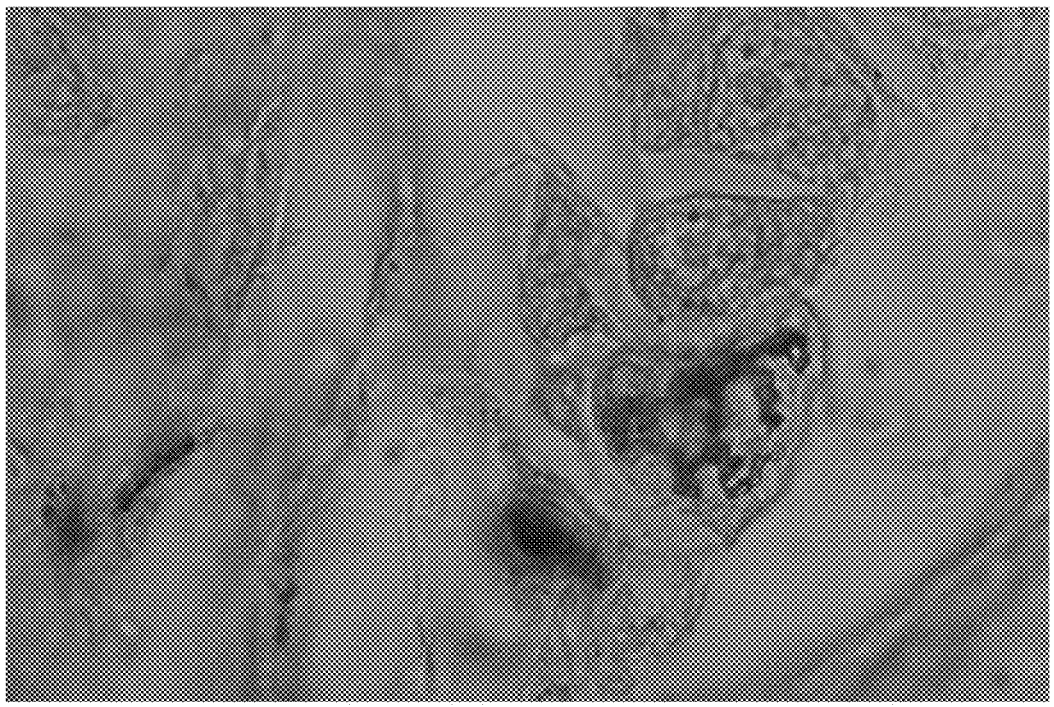
FIG. 4 shows a microscopic image of a number of cells stained in accordance with a method of staining cells in accordance with the invention, the microscopic image shows a nucleus of a breast cancer cell in the anaphase, the microscopic image was captured from a light microscope at 40× magnification using an oil lens.
Figure 5:
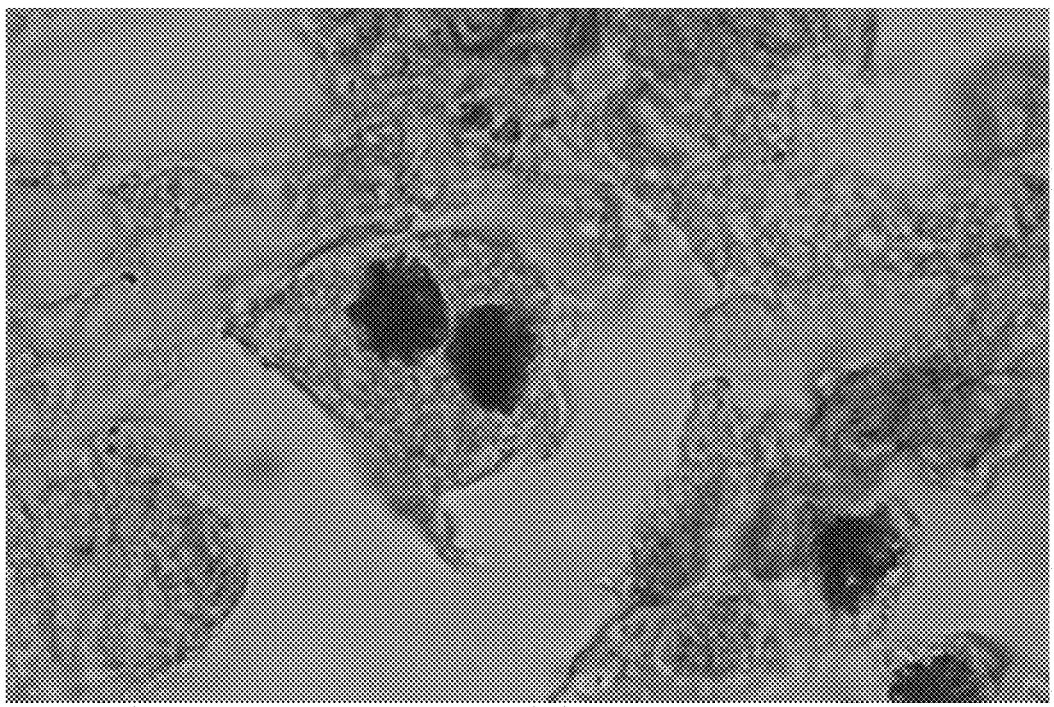
FIG. 5 shows a microscopic image of a number of cells stained in accordance with a method of staining cells in accordance with the invention, the microscopic image shows a nucleus of a breast cancer cell in the telophase, the microscopic image was captured from a light microscope at 40× magnification using an oil lens.
Figure 6:
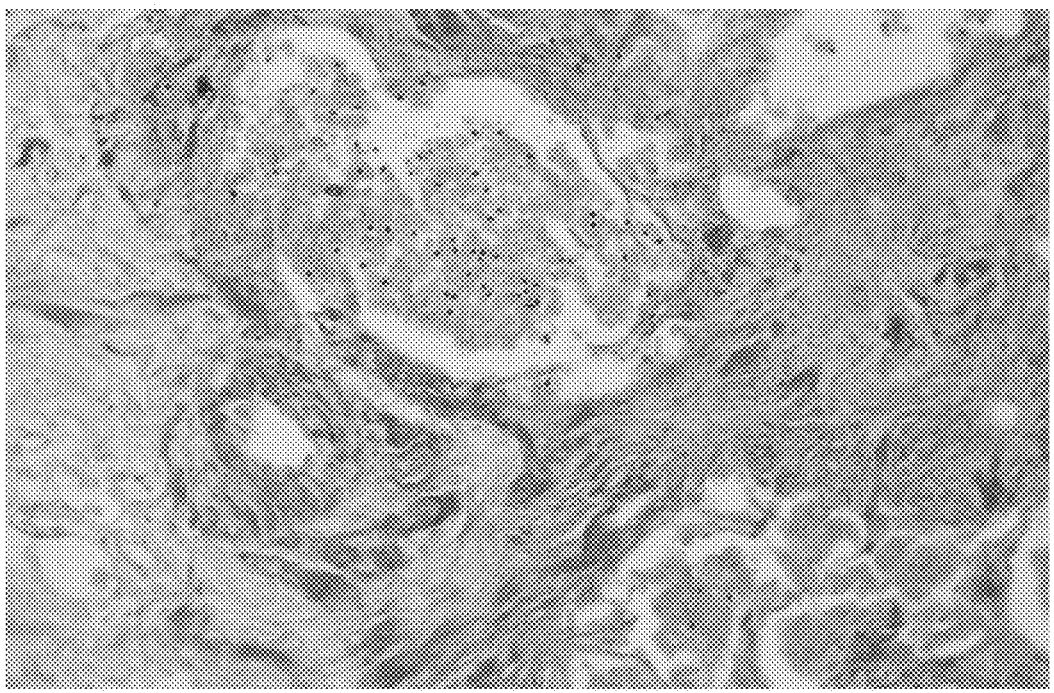
FIG. 6 shows a microscopic image of a number of cells stained in accordance with a method of staining cells in accordance with the invention, the microscopic image shows mitosis cells (dark spots in the duct) in a section of invasive ductile carcinoma, the cancer cells in the rest period appear yellow color, the microscopic image was captured from a light microscope at 40× magnification using an oil lens.
Figure 7:
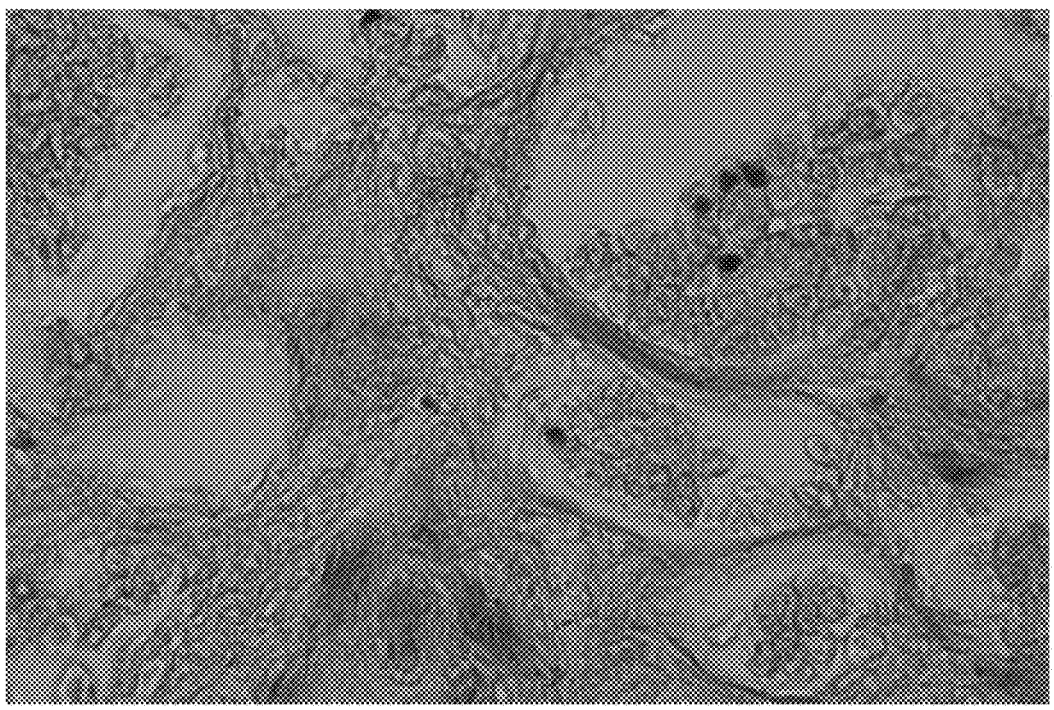
FIG. 7 shows a microscopic image of a number of cells stained in accordance with a method of staining cells in accordance with the invention, the microscopic image shows mitosis cells (dark spots) in a section of invasive ductile carcinoma, the cancer cells in the rest period appear yellow color, the microscopic image was captured from a light microscope at 40× magnification using an oil lens.
Figure 8:
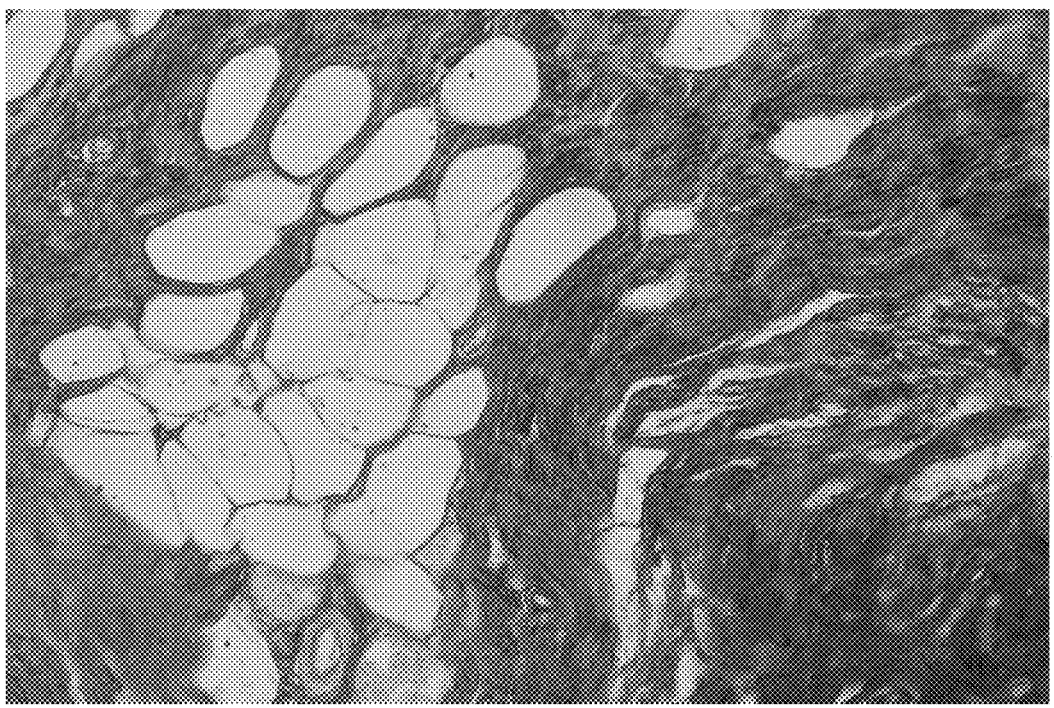
FIG. 8 shows a microscopic image of a number of cells stained in accordance with a method of staining cells in accordance with the invention, the microscopic image shows collagen fibers and also adipose tissue, there is no activity of mitosis cells in a this section (invasive ductile carcinoma), the cancer cells in the rest period appear yellow in a color, the microscopic image was captured from a light microscope at 40× magnification using an oil lens.
Figure 9:
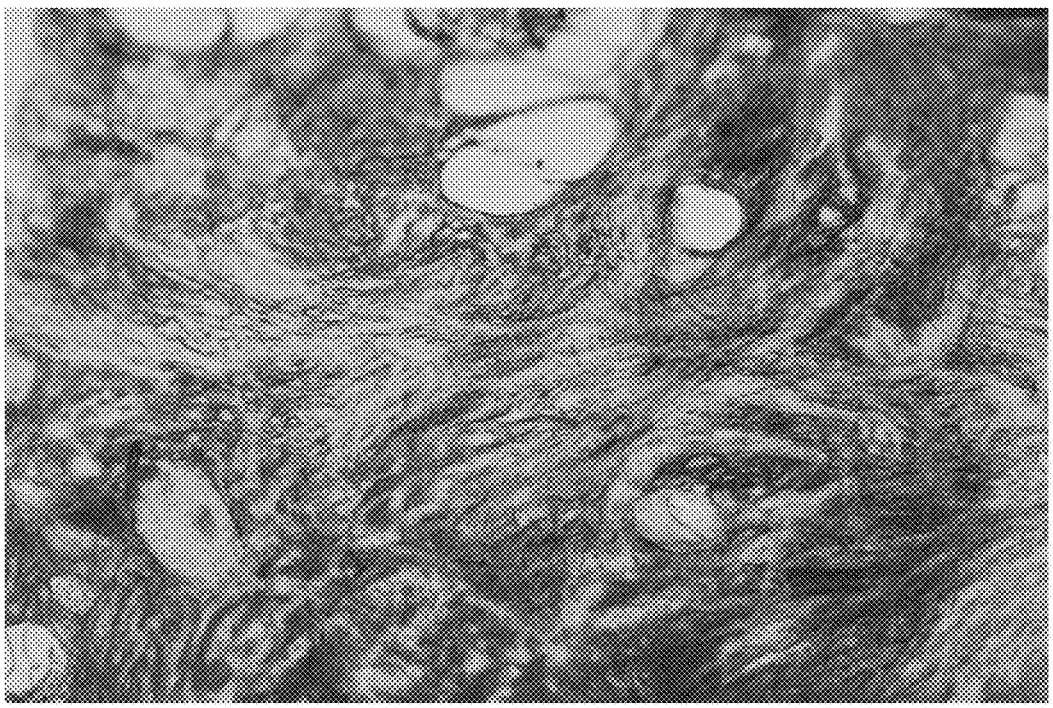
FIG. 9 shows a microscopic image of a section of a number of breast cancer cells stained in accordance with a method of staining cells in accordance with the invention, the microscopic image shows two types of fibers, the deep pink to red fibers are collagen fibers and the yellow fibers are elastic fibers, the microscopic image was captured from a light microscope at 40× magnification using an oil lens.
Figure 10:
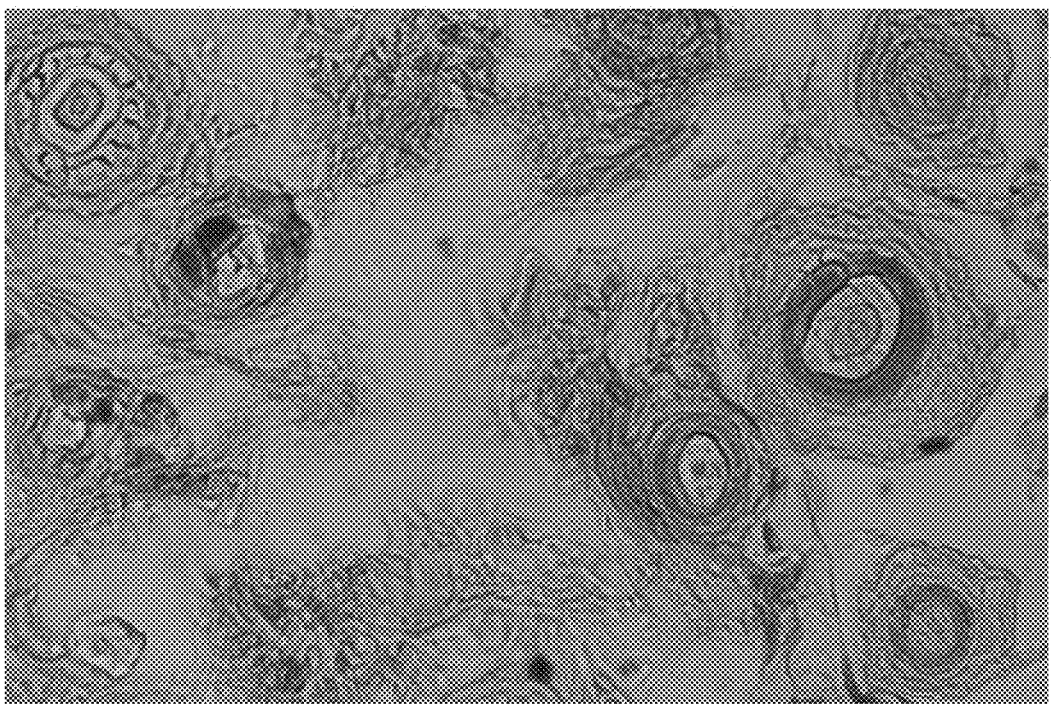
FIG. 10 shows a microscopic image of a number of cells stained in accordance with a method of staining cells in accordance with the invention, the microscopic image shows a section of a rat's skin, showing the hair follicle with its layers in two different color, the microscopic image was captured from a light microscope at 40× magnification using an oil lens.
Figure 11:
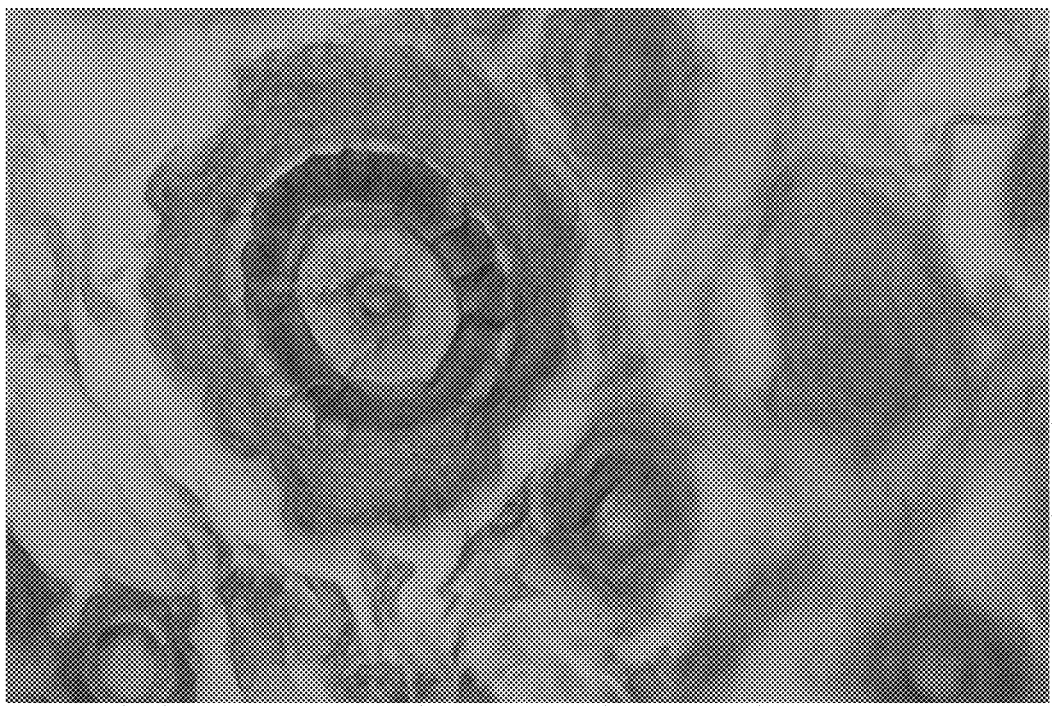
FIG. 11 shows a microscopic image of a number of cells stained in accordance with a method of staining cells in accordance with the invention, the microscopic image shows a section of a rat's skin, and shows the hair follicle with its layers in two different color, the microscopic image was captured from a light microscope at 40× magnification using an oil lens.
Figure 12:
FIG. 12 shows a microscopic image of a number of cells stained in accordance with a method of staining cells in accordance with the invention, the microscopic image shows a section of a rat's skin, showing the striations of muscle cells in the subcutaneous layer, the microscopic image was captured from a light microscope at 40× magnification using an oil lens.
Figure 13:
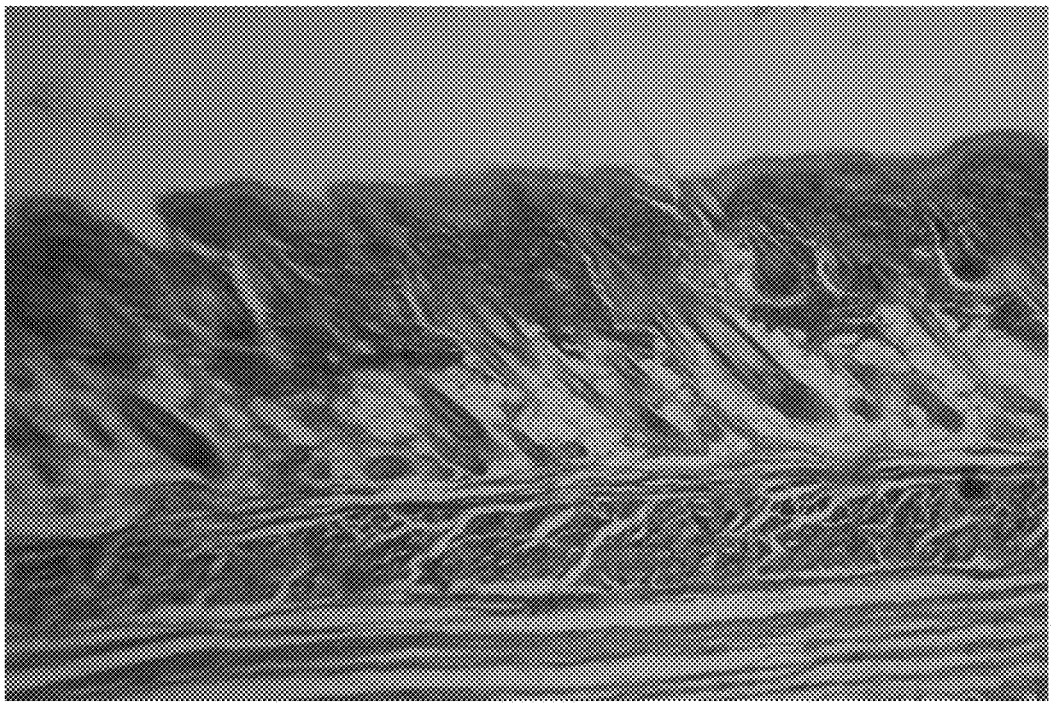
FIG. 13 shows a microscopic image of a number of cells stained in accordance with a method of staining cells in accordance with the invention, the microscopic image shows a section of a rat's skin, and shows the layers of skin with hairs stained yellow in color, the microscopic image was captured from a light microscope at 40× magnification using an oil lens.
Figure 14:
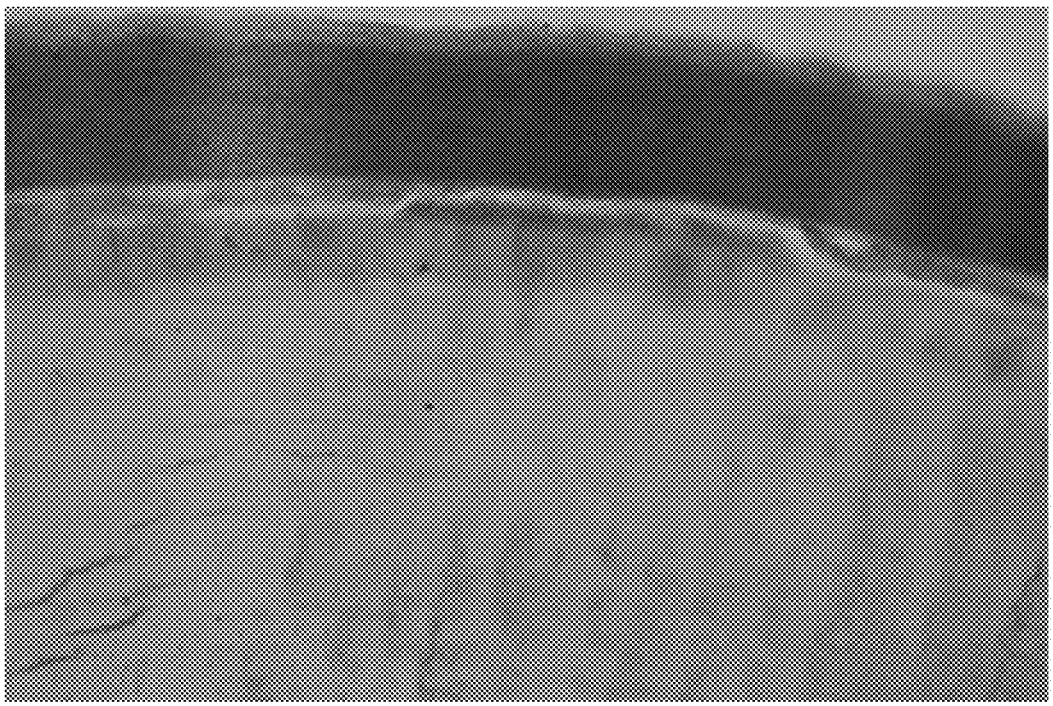
FIG. 14 shows a microscopic image of a number of cells stained in accordance with a method of staining cells in accordance with the invention, the microscopic image shows a section of a rat's eye, with the lens stained in a yellow color and the other layers stained in a pink color, the microscopic image was captured from a light microscope at 40× magnification using an oil lens.
Figure 15:
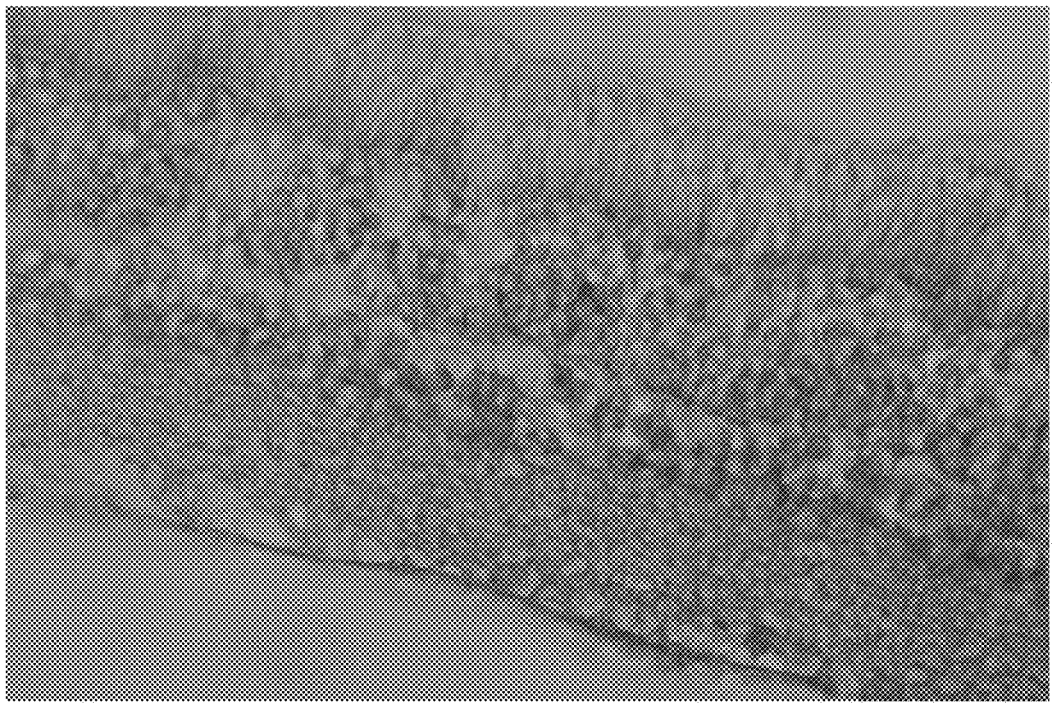
FIG. 15 shows a microscopic image of a number of cells stained in accordance with a method of staining cells in accordance with the invention, the microscopic image shows a section of a rat's eye, and shows photoreceptors in the retina with the rods and cones stained in different colors, the microscopic image was captured from a light microscope at 40× magnification using an oil lens.

As shown in FIGS. 8 and 9 of the drawings, the staining method described hereinabove stains the collagen fibers in sections of both malignant and benign tumors.

In all tumor sections (malignant or benign), the stain stained the collagen fibers a deep pink color. Additionally, another type of fibers, which are elastic fibers, appeared yellow in color as shown in FIG. 9.

As shown in FIGS. 9 to 15 and 16A, 16B and 16C of the drawings, the staining method described hereinabove stains normal rat tissues of the skin, brain, kidney, lachrymal glands, heart, spleen, liver, eye and small intestine.

Referring to FIGS. 9 to 13 of the drawings, with normal skin tissue the stain showed the hair shaft very well; it appeared yellow in color because of the presence of keratin, which is also seen in epidermal surface hyperkeratosis.

Figure 16A:
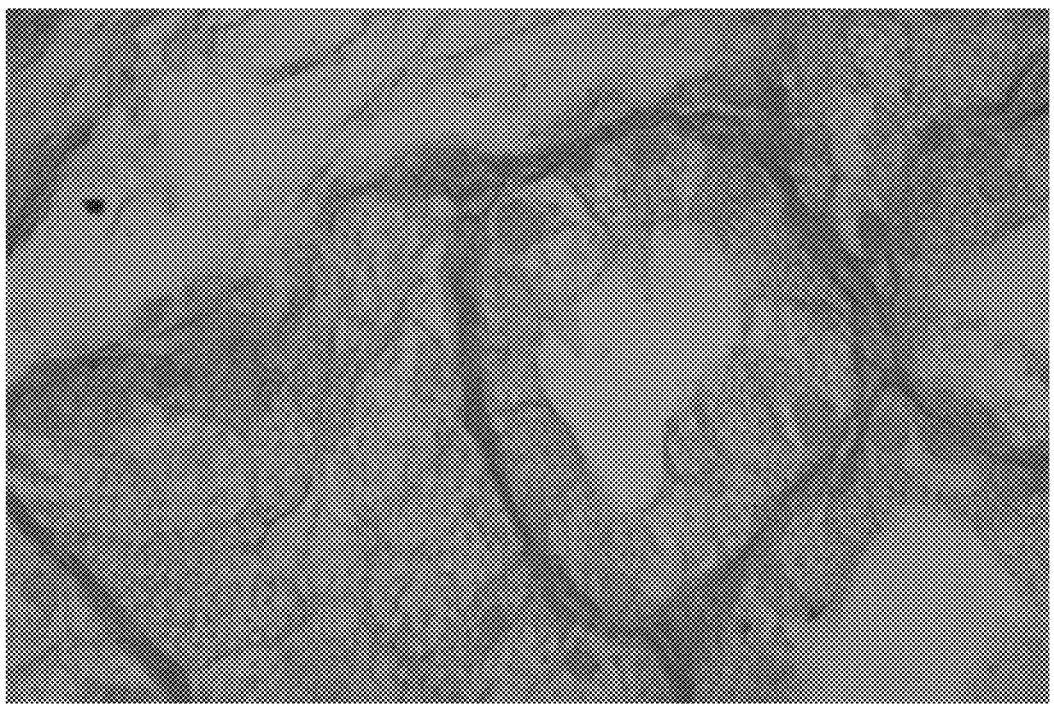
FIG. 16A shows a microscopic image of a number of cells stained in accordance with a method of staining cells in accordance with the invention, the microscopic image shows a section of a rat's lachrymal gland and shows the stained basement membrane, the microscopic image was captured from a light microscope at 40× magnification using an oil lens.
Figure 16B:
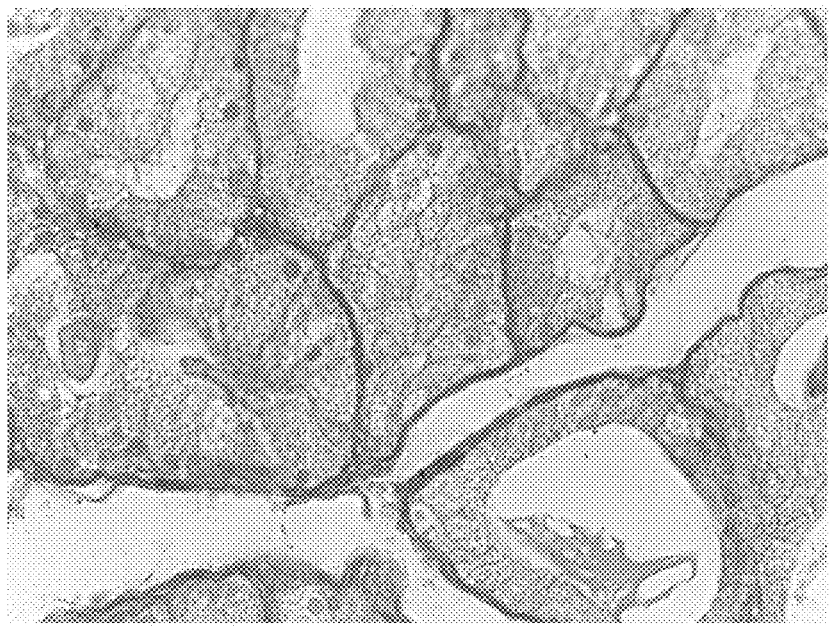
FIG. 16B shows a microscopic image of a number of cells stained in accordance with a method of staining cells in accordance with the invention, the microscopic image shows a section of a rat's lachrymal gland and shows the stained basement membrane, the microscopic image was captured from a light microscope at 40× magnification using an oil lens.
Figure 16C:
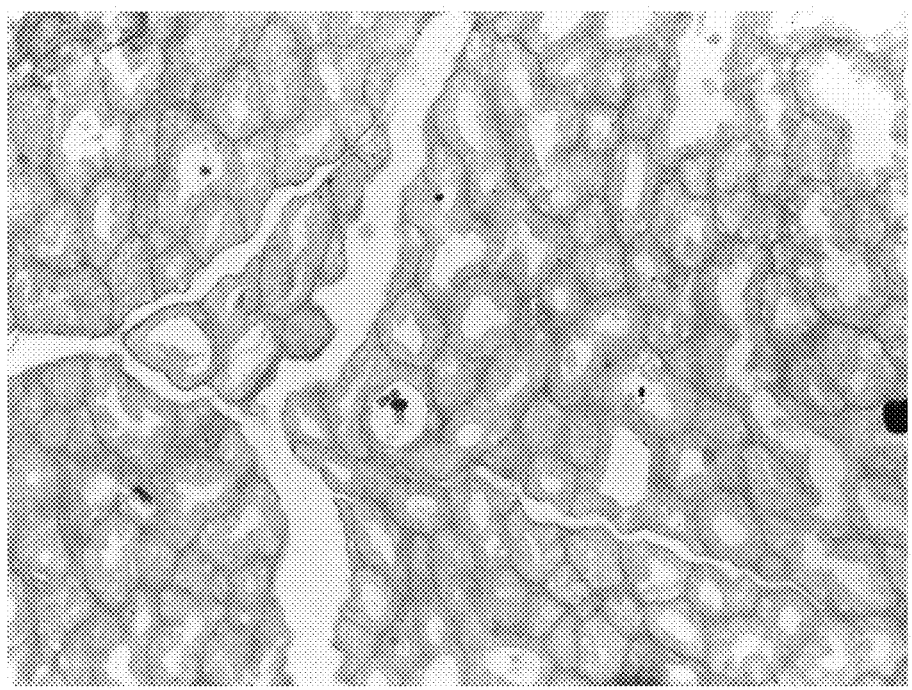
FIG. 16C shows a microscopic image of a number of cells stained in accordance with a method of staining cells in accordance with the invention, the microscopic image shows a section of a rat's lachrymal gland and shows the stained basement membrane, the microscopic image was captured from a light microscope at 10× magnification using an oil lens.

The stain stained the basement membranes in the kidney and the lachrymal gland tissue sections, as shown in FIGS. 16A, 16B and 16C. It also stained some of the collagen fibers with a pink color.

Concentrations of 5% and 10% phosphotungistic acid both gave good results for staining collagen fibers.

Concentrations of 5% and 10% phosphomolybdic acid only stained mitotic nuclei, but not collagen fibers.

3. Muscle

The stain was also found to stain skeletal muscle striations. In the subcutaneous tissue, the striations in the muscle were very clear, as can be seen from FIG. 12 of the drawings.

Observations

The stain provides a stronger and cleaner visual signal. Additionally, it is very easy to work with, and can be used for mitotic nuclei and collagen fibers. It is easily available the world over and very cheap. This stain costs approximately US $10 compared with the commercial kits available at present, such as the K167 kit or the anti-phosphohistone H3 stain that costs more than US $400.

The Applicant envisages that the stain may therefore form part of a stain kit/diagnosis kit which includes the stain as described and defined herein. The invention extends to a stain kit/diagnosis kit including the stain as described and defined herein.

Advantageously, all chemical agents used as described hereinabove are readily accessible, cheap to obtain and are not dangerous. The stain has been found to be quick to prepare and has a long shelf life. More specifically, the shelf life is approximately 12 months when stored in a refrigerator or at a temperature of 30° C.

Advantageously, the time required to stain tissue samples is relatively short when compared to the time required for staining tissue samples using other known methods of staining samples.

The stain is particularly useful for staining mitotic figures. More particularly, the stain is effective in sufficiently staining the mitotic figures to facilitate accurate counting of the mitotic figures. More specifically, the Applicant envisages that the stain in accordance with the invention provides a new stain for detecting and counting mitotic figures in paraffin sections of human breast cancer and other cancers and furthermore provides a new stain for staining collagen fibers.

Figure 17:
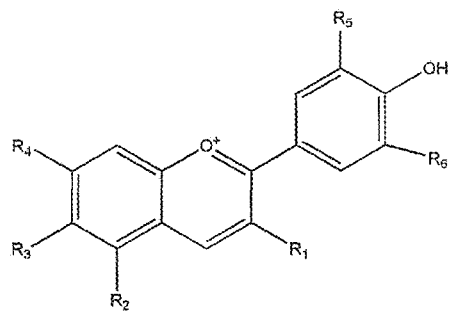
FIG. 17 shows the chemical structure of anthocyanins.

Without wishing to be bound by any particular theory, the Applicant believes that the staining properties of the stain in accordance with the invention can be attributed to anthocyanins present within the petunia petals and which are the largest group of water-soluble pigments in the plant kingdom, known collectively as flavonoids. FIG. 17 shows the general chemical structure of anthocyanins, wherein $R_1$=—OH; $R_2$=—OH (or) —OCH$_3$, $R_3$=—OH (or) —H; $R_4$=—OH (or) —OCH$_3$; $R_5$=—H (or) —OH (or) —OCH$_3$; and $R_6$=—H (or) —OH (or) —OCH$_3$.

Chemically, anthocyanins are based on a C15 skeleton with a chromane ring bearing a second aromatic ring B in position 2 (C6-C3-C6) with one or more sugar molecules bonded at different hydroxylated positions of the basic structure. Anthocyanins are substituted glycosides of salts of phenyl-2-benzopyrilium anthocyanins.

Anthocyanins can be found in different chemical forms, depending on the pH of the solution: at pH 1, the flavylium cation (red color) is the predominant species and contributes to purple and red colors, whereas at pH 2-4, the blue quinoidal species are predominant.

The anthocyanins constitute the pigment of the petunia petals flowers and are found in different colors such as, for example, purple and light blue. The color of some petunia flowers can be attributed to the presence of cyanidin and malvidin containing anthocyanins. The color of other petunia flowers can be attributed to the presence of delphinidin containing anthocyanins.

Without wishing to be bound by any particular theory, the Applicant envisages that the crude pigment of anthocyanins changed color from blue to deep red when mixed with saturated solution of picric acid.

Figure 18:
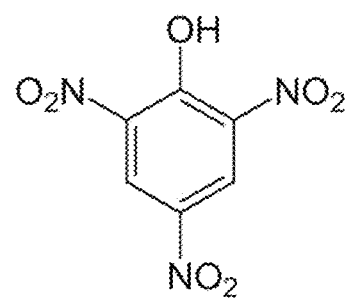
FIG. 18 shows the chemical structure of picric Acid.
Figure 19:
FIG. 19 shows a blue flower of a petunia.
Figure 20:
FIG. 20 shows a purple flower of a petunia.
Figure 21:
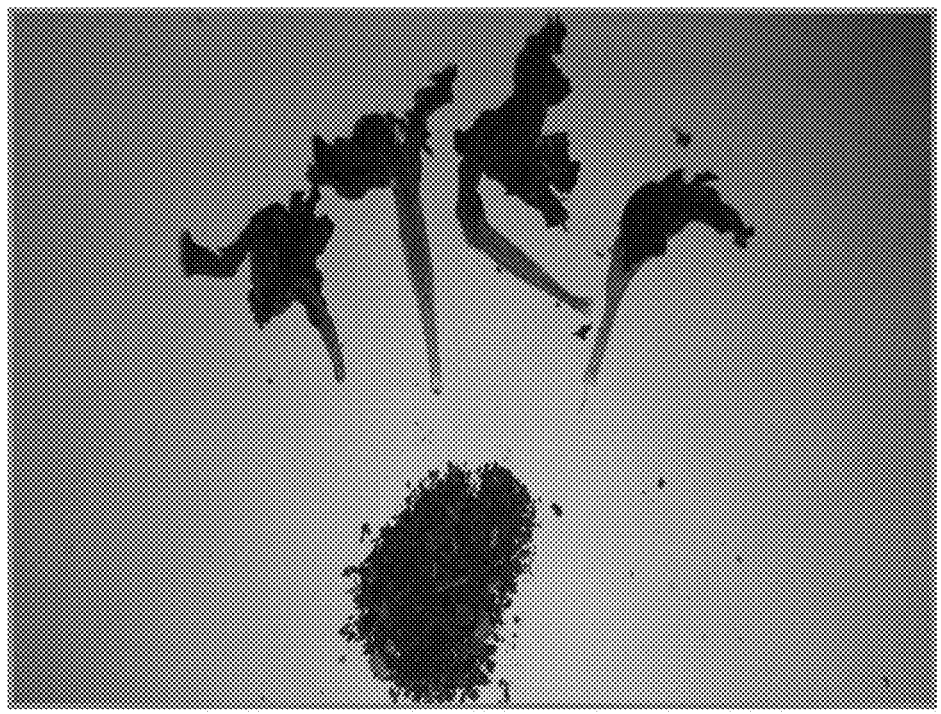
FIG. 21 shows a dried flower of blue petunia as well as crushed particles formed from the dry flower.

Picric acid ($C_6H_3N_3O_7$) is most commonly seen in its yellow, water-soluble, crystalline form and is considered an acidic coagulant, which changes the charges on ionizable side chains such as (—NH2→NH3+) and (COO→COOH) of proteins, disrupts electrostatic and hydrogen bonding, and inserts a lipophilic anion into the non-hydrophilic region, thereby disrupting the tertiary structure of proteins. The chemical structure of picric Acid is shown in FIG. 18.

Without wishing to be bound by any particular theory, the Applicant envisages that the crude pigment of anthocyanins changed color from blue to deep red when mixed with saturated solution of picric acid, specifically because of the changes to the H ion sites, and envisages that this reaction could change the anthocyanin to anthocyanidin by remove the sugar group. The Applicant envisages that the stain in accordance with the invention is thus a cation.

Without wishing to be bound by any particular theory, the Applicant envisages that, when the sections of breast cancer and other cancers and normal rat tissues such as samples of skin, eye, small intestine, etc. were rinsed in 10% solution of phoshotungistic acid, the important role of phoshotungistic acid comes from the electron density of phoshotungistic acid (which arises from the presence of the 12 tungsten atoms), it acts as a negative stain and bind to, alternatively, are adsorbed onto specific parts of the tissue, such as nuclei and collagen fibers, alternatively, or additionally, they could also block other sites.

Alternatively, without wishing to be bound by any particular theory, the Applicant envisages that the activity could be due to the tungsten atoms that act as a mordant to bind the dye to the nucleus or collagen fibers.

Without wishing to be bound by any theory, the Applicant envisages that one of the negatively charged chemical groups present in a tissue section is phosphate, which are associated with DNA and RNA. Phosphate groups are weak acids, and hence become protonated (not ionized) if the concentration of protons (hydrogen ions) is high enough. Typically, this occurs below pH 2.5. The phosphates of nucleic acids are fully ionized at pH 3.5-4. A basic dye at pH 3-4 stains nuclei, and so the phosphate groups in tissue sections are protonated when they are rinsed with phoshotungistic acid (10%) solution. The protonation increases further when the sections are stained with the red stain that is generated from the reaction between solutions anthocyanins and picric acid.

The invention claimed is:

1. A method of making a staining composition for staining one or more cells, the staining composition consisting of an extract of petunia petals, picric acid, and an aqueous medium, the method comprising:
combining the extract of petunia petals and the picric acid in the aqueous medium to chemically react the extract with the picric acid to form a staining composition in the form of a solution.

2. The method as claimed in claim 1, wherein the extract of petunia petals is formed by at least partially dissolving the petunia petals in an aqueous medium.

3. The method as claimed in claim 2, wherein the petunia petals are dried petunia petals.

4. The method as claimed in claim 3, wherein the dried petunia petals are obtained by providing a predetermined mass of fresh wet petunia petals and drying the petunia petals until a mass of the dried petunia petals is 10% of said predetermined mass of the fresh wet petunia petals.

5. The method as claimed in claim 4, wherein the staining composition includes at least 60 mg of picric acid per gram of the dried petunia petals.

6. The method as claimed in claim 4, wherein the staining composition includes between 200 mg to 400 mg of picric acid per gram of the dried petunia petals.

7. The method as claimed in claim 1, wherein the aqueous medium is water.

8. The staining composition formed by the method of making a staining composition as claimed in claim 1.

9. The staining composition as claimed in claim 8, wherein the staining composition selectively stains only nuclei of cells undergoing mitosis while not staining nuclei without mitotic activity.

\* \* \* \* \*